(12) United States Patent
Xu et al.

(10) Patent No.: US 11,746,063 B2
(45) Date of Patent: Sep. 5, 2023

(54) SULFATE CORROSION-RESISTANT CONCRETE AND METHOD THEREOF FOR OPTIMIZING PROPORTION AND APPLICATION

(71) Applicant: Research Institute of Highway Ministry of Transport, Beijing (CN)

(72) Inventors: Chongbang Xu, Beijing (CN); Xuefeng Li, Beijing (CN); Hualao Wang, Beijing (CN); Xiaojing Gao, Beijing (CN)

(73) Assignee: RESEARCH INSTITUTE OF HIGHWAY MINISTRY OF TRANSPORT, Beijing (CN)

( * ) Notice: Subject to any disclaimer, the term of this patent is extended or adjusted under 35 U.S.C. 154(b) by 0 days.

(21) Appl. No.: 17/952,798

(22) Filed: Sep. 26, 2022

(65) Prior Publication Data
US 2023/0129027 A1    Apr. 27, 2023

(30) Foreign Application Priority Data
Oct. 21, 2021 (CN) .......................... 202111225527.0

(51) Int. Cl.
*C04B 40/00* (2006.01)
*C04B 14/14* (2006.01)
(Continued)

(52) U.S. Cl.
CPC .......... *C04B 40/0096* (2013.01); *C04B 14/14* (2013.01); *C04B 14/28* (2013.01);
(Continued)

(58) Field of Classification Search
CPC ..... C04B 40/0096; C04B 14/14; C04B 14/28; C04B 22/142; C04B 24/2641; C04B 28/04; G01N 23/20; G01N 33/383
See application file for complete search history.

(56) References Cited

FOREIGN PATENT DOCUMENTS

| CA | 2815799 A1 | 5/2012 |
|---|---|---|
| CN | 105236854 A | 1/2016 |

(Continued)

OTHER PUBLICATIONS

Nadir et al. The Mechanisms of Sulphate Attack in Concrete—A Review. Modern Approaches on Material Science. vol. 5, Issue 2, pp. 658-670. (Year: 2022).*

(Continued)

*Primary Examiner* — John E Uselding
(74) *Attorney, Agent, or Firm* — Stuart H. Mayer; Mayer & Williams PC

(57) ABSTRACT

Disclosed is a sulfate corrosion-resistant concrete, a method for optimizing proportion and application thereof. The concrete is formed by mixing and stirring base stocks, aggregates, admixtures, external additives and water. The base stock of the concrete is 17.4-17.5 parts of Portland cement; the aggregates include 38.9 parts of basalt with aggregate size of 5-10 mm and 33.1-33.2 parts of basalt medium sand; the admixtures are 1.9-1.95 parts of silica fume or fly ash, and further including 0.23-0.24 part of polycarboxylate water reducer and 1.34-1.35 part of sulfate corrosion-resistant liquid preservative. Optimized proportion method: according to the corrosion characteristics of sulfate and corrosion environment parameters, determine the composition and proportion of basic samples and comparison samples, make and cure sample components, test the deep components of the samples, and obtain the optimal composition and proportion according to the test results.

4 Claims, 28 Drawing Sheets

(51) Int. Cl.
*C04B 14/28* (2006.01)
*C04B 18/08* (2006.01)
*C04B 22/14* (2006.01)
*C04B 24/26* (2006.01)
*C04B 28/04* (2006.01)
*G01N 23/20* (2018.01)
*G01N 33/38* (2006.01)
*C04B 103/30* (2006.01)
*C04B 111/20* (2006.01)

(52) U.S. Cl.
CPC ............ *C04B 18/08* (2013.01); *C04B 22/142* (2013.01); *C04B 24/2641* (2013.01); *C04B 28/04* (2013.01); *G01N 23/20* (2013.01); *G01N 33/383* (2013.01); *C04B 2103/302* (2013.01); *C04B 2111/2015* (2013.01); *G01N 2223/056* (2013.01); *G01N 2223/60* (2013.01)

(56) References Cited

FOREIGN PATENT DOCUMENTS

| | | | |
|---|---|---|---|
| CN | 108414428 A | | 8/2018 |
| CN | 110563369 A | * | 12/2019 ......... C04B 20/1033 |
| CN | 110563399 A | | 12/2019 |
| CN | 110668749 A | | 1/2020 |
| CN | 110922125 A | | 3/2020 |
| CN | 112098308 A | | 12/2020 |
| JP | 2008201656 A | | 9/2008 |

OTHER PUBLICATIONS

Fengchen et al. Effect of Fly Ash on TSA Resistance of Cement-based Material. Journal of Wuhan University of Technology-Mater. Sci. Ed. Jun. 2011. p. 561-566 (Year: 2011).*
English machine translation of CN110563369A (Year: 2019).*

* cited by examiner

SULFATE CORROSION-RESISTANT CONCRETE AND METHOD THEREOF FOR OPTIMIZING PROPORTION AND APPLICATION

CROSS-REFERENCE TO RELATED APPLICATIONS

This application claims priority to Chinese Patent Application No. 202111225527.0, filed on Oct. 21, 2021, the contents of which are hereby incorporated by reference.

TECHNICAL FIELD

The invention relates to a sulfate corrosion-resistant concrete and its application in the engineering field, and in particular to a sulfate corrosion-resistant concrete and its method for optimizing proportion and an application.

BACKGROUND

Thaumasite-type sulfate corrosion is a special concrete service environment, in which tunnel lining with ordinary concrete will be corroded by sulfate in rock mass. The existing research shows that under the conditions of sulfate, water and a certain temperature, thaumasite-type sulfate will corrode cement-based concrete (TSA) containing limestone powder or limestone admixture and destroy its gel properties. It has also been explained in the background technology of No. 20110192758.6 patent entitled thaumasite-type sulfate corrosion inhibitor and its preparation method, that for the thaumasite-type sulfate corrosion, ordinary corrosion-resistant concrete can't achieve the corrosion-resistant effect, and special corrosion-resistant concrete can play a role in corrosion resistance. However, the ingredients and technology of the special corrosion-resistant concrete are complicated with cumbersome manufacture process and high transportation costs, so the special corrosion-resistant concrete is not suitable for practical engineering.

The principle of inhibitor is to form a coating on the concrete surface to inhibit the corrosion reaction. However, the inhibitor has poor applicability in some tunnel projects under special working conditions, mainly because the tunnel concrete surface, especially the initial support, which is not a flat surface, and it is difficult to generate an effective coating.

In practical engineering, the concrete of tunnel lining suffers from more complicated corrosion, one is the external corrosion conditions formed by surrounding rock mass and groundwater, the other is the water seepage and corrosion inside the concrete itself. For example, in Taihang Mountain area of North China, there is also a thaumasite-type sulfate corrosion, but this area is a gypsum rock stratum with weak water permeability, and the water seepage amount and corrosion conditions are different from those of ordinary thaumasite-type sulfate corrosion. However, the existing thaumasite-type sulfate corrosion tests are mostly aimed at the formation mechanism and related parameters of thaumasite, and are mostly used for indoor theoretical research and analysis. In view of the lack of scientific and effective proportioning research on the corrosion in the actual engineering environment, the basic research needs relevant proportioning tests and the research on the components and contents in the tests to be applied to engineering practice. Therefore, the basic tests need to be combined with optimizing proportion tests to achieve technical results in practical application.

Therefore, it is urgent to develop a sulfate corrosion-resistant concrete, its method for optimizing proportion and application, which have good economic benefits and industrial application potential.

SUMMARY

Specifically the invention provides a sulfate corrosion-resistant concrete and its method for optimizing proportion and an application, and reveals the theoretical and experimental basis of corrosion-resistant concrete in practical engineering application.

To achieve the above objective, the present invention provides the following technical scheme:

a sulfate corrosion-resistant concrete, wherein the concrete is formed by mixing and stirring base stocks, aggregates, admixtures, external additives and water, and the components and mass fractions of the concrete obtained by the method for optimizing proportion are as follows:

the base stocks are 17.4-17.5 parts of Portland cement with a strength grade of 42.5;

the aggregates comprise fine aggregates and coarse aggregates, wherein the coarse aggregates are 38.9 parts of basalts with a particle size of 5-10 mm, and the fine aggregates are 33.1-33.2 parts of basalt medium sand;

the admixtures are 1.9-1.95 parts of silica fume or fly ash with total activity greater than 80%;

6.9-7 parts of water;

the external additives are a liquid preservative and a water reducer, the water reducer is 0.23-0.24 part of polycarboxylate water reducer, and the liquid preservative is 1.34-1.35 parts of sulfate corrosion-resistant liquid preservative.

A method for optimizing proportion of sulfate corrosion-resistant concrete, which includes the following steps:

(1) determining compositions and a proportion of basic sample and comparison sample according to the corrosion characteristics of sulfate and corrosion environment parameters;

(2) making sample components according to different components and proportions, and carrying out 28-day basic cure, which comprises ordinary cure and special cure;

(3) considering the influence of external carbonate ions, setting two samples with the same composition and proportion, and curing the two samples by standard cure and low-temperature cure respectively;

(4) respectively recording the cure data of the sample in different curing periods;

(5) observing appearances of the samples, and performing XRD (X-Ray Diffraction) test to test the deep components of the samples; and (6) comparing test results and obtaining an optimal composition and proportion of corrosion-resistant concrete according to the test results;

in the step (3), the standard cure is at room temperature of 20° C., and a magnesium sulfate solution and limestone powder aqueous solution with 10% concentration are used for a flowing infiltration to reach a relative humidity of 95%;

the low-temperature cure in the step (3) is that the samples are placed in a solution with a temperature of 4-6° C. for an immersion cure, and the solution is a mixed solution of the limestone powder aqueous solution with 10% concentration and the magnesium sulfate solution;

In the step (1), common samples, optimized cement samples, optimized proportion samples, optimized proportion-optimized cement samples, internally prepared sulfate ion samples, optimized proportion considering carbonate ion intrusion samples and optimized cement considering carbonate ion intrusion samples are respectively set according to a thaumasite-type sulfate corrosion.

In an embodiment, as an improvement, the components of the sample in the step (1) are set as follows:

the components of the common sample are as follows: P.O cement with a strength of 42.5, water, fly ash, limestone, basalt medium sand, liquid preservative and water reducer;

the components of the optimized cement sample are that: based on the common sample, replace the cement in the common sample with P.I cement with a strength of 42.5;

the components of the optimized proportion sample are as follows: P.O cement with a strength of 42.5, water, fly ash, basalt, basalt medium sand, liquid preservative and water reducer;

the components of optimized proportion-optimized cement sample are that: based on the optimized proportion sample, replace the cement in the optimized proportion sample with P.I cement with a strength of 42.5;

the components of the internally prepared sulfate ion sample are as follows: P.O cement with a strength of 42.5, water, limestone powder, limestone, medium sand and water reducer.

In an embodiment, as an improvement, the proportions of the samples are as follows:

the mass fractions of the common sample are as follows: 393 parts of P.O cement with strength of 42.5, 200 parts of water, 48 parts of fly ash, 934 parts of limestone, 796 parts of medium sand, 32.5 parts of liquid preservative, 3.84 parts of water reducer, and the water-binder ratio is 0.45;

the mass fractions of the optimized proportion-optimized cement sample are that: based on the common sample, replace the cement in the common sample with 393 parts of P.I cement with a strength of 42.5;

the mass fractions of the optimized proportion sample are as follows: 422 parts of P.O cement with strength of 42.5, 168 parts of water, 47 parts of fly ash, 940 parts of basalt, 801 parts of medium sand, 32.5 parts of liquid preservative, 5.64 parts of water reducer, and the water-binder ratio is 0.36;

the mass fractions of optimized proportion-optimized cement sample are that: based on the optimized proportion sample, replace the cement in the optimized proportion sample with 422 parts of P.I cement with a strength of 42.5;

the mass fractions of the internally prepared sulfate ion sample are as follows: 422 parts of P.O cement with strength of 42.5, 190 parts of water, 47 parts of limestone powder, 864 parts of limestone, 974 parts of medium sand, 5.64 parts of water reducer, and the water-binder ratio is 0.35;

In the 28-day basic cure of the above samples, ordinary cure with water solution spraying is adopted;

the optimized proportion considering carbonate ion intrusion sample means that the optimized proportion sample is performed spray cure by using the limestone powder aqueous solution with 10% concentration during the 28-day basic cure, and the spray cure is a special cure;

the optimized cement considering carbonate ion intrusion sample means that the optimized proportion-optimized cement sample is performed spray cure by using the limestone powder aqueous solution with 10% concentration during the 28-day basic cure, and the spray cure is a special cure;

In the present invention, as an improvement, the curing time in step (4) is 1 month, 3 months, 6 months, 9 months and 12 months respectively.

A tunnel lining design method using the sulfate corrosion-resistant concrete, wherein the tunnel lining is designed in a full-ring closed form, the surrounding rock of the lining is blocked from water by grouting; the seepage resistance grade of the corrosion-resistant concrete of the primary lining of the tunnel is greater than P6, the seepage resistance grade of the corrosion-resistant concrete of the secondary lining is greater than P8, and the corrosion-resistant coefficient of the corrosion-resistant concrete in the lining is greater than 0.8.

Compared with the prior art, the invention has the advantages that:

(1) simulating the actual proportioning test of the project, combining with the special corrosive environment of weak water permeability gypsum rock stratum, reappearing the whole process of sulfate erosion and analyzing the causes of erosion, providing theoretical basis for the selection and composition design of corrosion-resistant concrete materials; the components and proportioning of samples in the test are set in combination with the current engineering situation and erosion characteristics.

(2) the composition and proportion of corrosion-resistant concrete in special stratum area are revealed through tests; in the comparative experiment of this application, the external sulfate corrosion is considered, and the influencing factors of carbonate ions are added according to the external corrosion environment, so as to make a comprehensive corrosion assessment for the actual engineering environment.

(3) through the test analysis and verification, the application is more concise and effective in preventing thaumasite-type sulfate corrosion, and it is convenient to obtain materials, without adding other expensive special materials, which is more conducive to engineering application and saving engineering cost; basalt aggregate is adopted, which is effective in maintaining the long-term performance of concrete structure strength and bearing capacity, and increases the durability of engineering structures.

BRIEF DESCRIPTION OF THE DRAWINGS

In order to more clearly explain the specific embodiment of the present invention or the technical solutions in the prior art, the following will briefly introduce the drawings that need to be used in the description of the specific embodiment or the prior art. In all drawings, similar elements or parts are generally identified by similar reference numerals. In the drawings, elements or parts are not necessarily drawn to actual scale.

DETAILED DESCRIPTION OF THE EMBODIMENTS

Figure 1A:
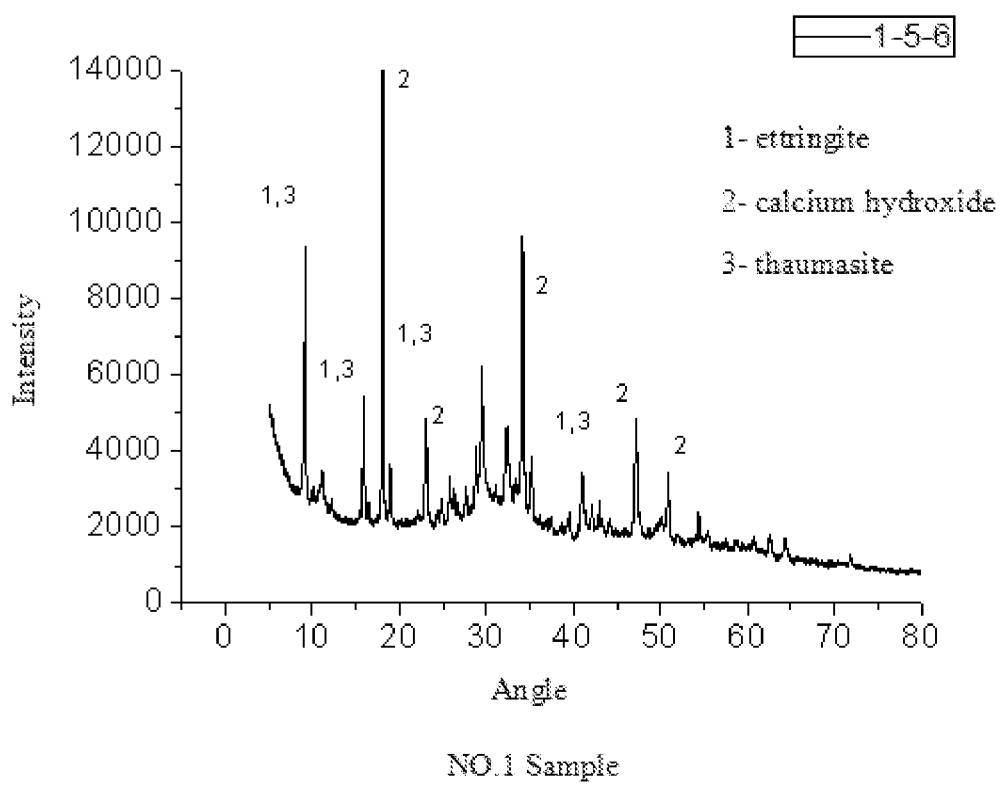
FIG. 1(a-g) is a structural schematic diagram of XRD test results of each sample at the age of 6 months in Embodiment 1 of the present invention.

The embodiment of the technical scheme of the present invention will be described in detail below with reference to the drawings. The following embodiments are only used to illustrate the technical scheme of the present invention more clearly, so they are only examples, and cannot be used to limit the scope of protection of the present invention.

The invention relates to a method for optimizing proportion of sulfate corrosion-resistant concrete. The first step of the optimization method is to determine the composition and proportioning of an optimized sample and a comparison sample according to the erosion characteristics of thaumasite-type sulfate and the corrosion environment parameters, which includes the following steps:

Step 1, according to the characteristics of thaumasite-type sulfate corrosion in existing study, the samples are considered from two aspects: external sulfate corrosion, and the generation of sulfate ions in concrete itself; the samples are set according to the following ways:

1) setting basic comparison samples;
2) setting samples containing no lime in cement and aggregate components;
3) the external additive is a sample which does not contain sulfate ions or can generate sulfate ions;
4) samples containing internal sulfate ion or external sulfate ion intrusion.

Step 2, there are 7 groups of basic samples and comparison samples, including common samples, optimized cement samples, optimized proportion samples, optimized proportion-optimized cement samples, internally prepared sulfate ion samples, optimized proportion samples considering carbonate ion intrusion and optimized cement samples considering carbonate ion intrusion. On the one hand, the setting of samples can reflect the influence of different components on erosion reaction, and on the other hand, the reaction process under different proportioning conditions by optimizing proportion, so as to achieve the best corrosion-resistant effect.

Step 3, determine the composition and proportion of the samples according to the test requirements of the samples and the actual corrosion environment and geological parameters of the project.

Common samples are commonly used components and proportions in tunnel lining engineering, and their proportions have not been adjusted according to sulfate corrosion. The components and proportions of common samples include 393 parts of P.O cement with strength of 42.5, 200 parts of water, 48 parts of fly ash, 934 parts of limestone, 796 parts of medium sand, 32.5 parts of liquid preservative, 3.84 parts of water reducer, and the water-binder ratio is 0.45;

According to the Step 1, based on common samples, as the optimized cement samples, P.O cement is replaced with 393 parts of P.I cement with the strength of 42.5.

The composition and proportion of the optimized proportion samples include 422 parts of P.O cement with strength of 42.5, 168 parts of water, 47 parts of fly ash, 940 parts of basalt, 801 parts of medium sand, 32.5 parts of liquid preservative, 5.64 parts of water reducer, and the water-binder ratio is 0.36. The content of cement and water is adjusted according to the water permeability characteristics of rock strata in corrosive environment to change the water-binder ratio. Meanwhile, the water-binder ratio affects sulfate erosion, so as to achieve objective of the required corrosion-resistant test;

Based on the optimized proportion samples, as optimized proportion-optimized cement samples, the cement in the optimized proportion sample is replaced with 422 parts of P.I cement with the strength of 42.5;

The proportion of internally prepared sulfate ion samples is as follows: 422 parts of P.O cement with strength of 42.5, 190 parts of water, 47 parts of limestone powder, 864 parts of limestone, 974 parts of medium sand, 5.64 parts of water reducer, and the water-binder ratio is 0.35. The components of the samples contain sulfate ions, so as to test the erosion effect of the samples from inside to outside.

The optimized proportion considering carbonate ion intrusion samples and the optimized cement considering carbonate ion intrusion samples reflect carbonate ion intrusion from the outside.

Step 2, making sample components according to different ingredients and proportions, and carrying out 28-day basic cure, which is divided into ordinary cure and special cure;

The common samples, the optimized cement samples, the optimized proportion-optimized cement samples and the internally prepared sulfate ion samples is carried out the basic cure of water solution spraying in the 28-day basic cure, which is a conventional cure;

The optimized proportion considering carbonate ion intrusion samples are that: the optimized proportion samples are sprayed and cured with 10% limestone powder aqueous solution in 28-day basic cure, which is a special cure, resulting in external carbonate ion intrusion;

The optimized cement considering carbonate ion intrusion samples are that: the optimized proportion-optimized cement samples are sprayed and cured with 10% limestone powder aqueous solution in 28-day basic cure, which is a special cure, resulting in external sulfate ion intrusion.

Step 3, considering the influence of external carbonate ions, setting two samples with the same composition and ratio, and the two samples are cured by standard cure and low-temperature cure respectively;

The standard cure is that at room temperature of 20° C., magnesium sulfate solution and 10% limestone powder aqueous solution are used for flowing infiltration to reach the relative humidity of 95%.

The low-temperature cure is that the samples is placed in a solution with a temperature of 4-6° C. for immersion cure, and the solution is a mixed solution of limestone powder aqueous solution with 10% concentration and magnesium sulfate solution;

The standard cure and low-temperature cure are the corrosion conditions of the lining in the actual engineering environment. The two curing methods simulate the corrosion environment in natural conditions and reproduce the corrosion process. In the gypsum rock stratum with weak water permeability, the corrosion of thaumasite-type sulfate will experience two conditions: room temperature and low temperature.

Step 4, recording the cure data of samples in different curing periods, in which the curing periods of recorded data are 1 month, 3 months, 6 months, 9 months and 12 months respectively.

Step 5, observing the appearance of the samples, and carrying out XRD test to test the deep components of the samples.

Step 4 and Step 5 are conventional test and detection steps of test data, and the required instruments and equipment are also existing equipment.

Step 6, comparing the test results and obtaining the optimal composition and proportion of corrosion-resistant concrete according to the test results; after comparing several groups of test data, finding out the optimal composition and proportion of corrosion-resistant concrete, and determining the composition and proportion of corrosion-resistant concrete used in the engineering according to the current situation of the engineering.

Through the above tests, the components and proportions of sulfate corrosion-resistant concrete for engineering under special conditions can be obtained. The concrete is made by mixing and stirring base stocks, aggregates, admixtures, external additives and water;

the base stocks are 17.4-17.5 parts of ordinary Portland cement with strength grade of 42.5;

the aggregate comprises fine aggregate and coarse aggregate, the coarse aggregate is basalt with a particle size of 5-10 mm, and the fine aggregate is basalt medium sand, including 38.9 parts of basalt and 33.1-33.2 parts of basalt medium sand;

the admixtures are 1.9-1.95 parts of silica fume or fly ash with total activity greater than 80%;

the external additives are liquid preservatives and water reducers which do not contain sulfate ions and do not generate sulfate ions, the water reducer is 0.23-0.24 part of polycarboxylate water reducer, and the liquid preservative is 1.34-1.35 parts of sulfate corrosion-resistant liquid preservative and 6.9-7 parts of water.

The tunnel lining design method using the sulfate corrosion-resistant concrete, wherein the tunnel lining is designed in a full-ring closed form, the surrounding rock of the lining is blocked from water by grouting; the seepage resistance grade of the corrosion-resistant concrete of the primary lining of the tunnel is greater than P6, the seepage resistance grade of the corrosion-resistant concrete of the secondary lining is greater than P8, and the corrosion-resistant coefficient of the corrosion-resistant concrete in the lining is greater than 0.8.

Embodiment 1

Taking the TSA failure process of Dugongling tunnel as an example, an experiment is set up according to the corrosion environment of sulfate corrosion on the concrete of the first branch of Dugongling tunnel.

The engineering geological condition of Dugongling Tunnel is limestone and gypsum rock stratum with weak water permeability. TSA damage is affected by groundwater, and it also damages the glue property of cement in concrete. Considering this geological condition and water permeability, the water-binder ratio is adjusted based on the existing concrete proportion, so as to realize the comparative corrosion-resistant test with the existing concrete proportion.

1. According to the damage characteristics of TSA, two kinds of cement and two kinds of stones are selected in the test to design the proportion. The cement is P.O42.5 and P.I42.5, and the stones are limestone and basalt. Considering the influence of external carbonate ion infiltration on the formation of thaumasite, the curing conditions of 10% limestone powder solution are designed, and seven concrete proportion samples are tested, including common samples, optimized cement samples, optimized proportion samples, optimized proportion-optimized cement samples, internally prepared sulfate ion samples, optimized proportion considering carbonate ion intrusion samples and optimized cement considering carbonate ion intrusion samples. See the following table for specific sample components and proportions:

TSA Test Scheme of Concrete

| NO. | P.O42.5 | P.I42.5 | Water | Fly ash | Water-binder ratio | basalt | Limestone | River sand | Liquid preservative | Water reducer | Magnesium sulfate reagent |
|---|---|---|---|---|---|---|---|---|---|---|---|
| 1 | 393 | / | 200 | 48 | 0.45 | / | 934 | 796 | 32.5 | 3.84 | 44.1 |
| 2 | / | 393 | 200 | 48 | 0.45 | / | 934 | 796 | 32.5 | 3.84 | 44.1 |
| 3 | 422 | / | 168 | 47 | 0.36 | 940 | / | 801 | 32.5 | 5.64 | 46.9 |
| 4 | / | 422 | 168 | 47 | 0.36 | 940 | / | 801 | 32.5 | 5.64 | 46.9 |
| 5 | 422 | / | 190 | Limestone powder47 | 0.35 | / | 864 | 974 | / | 5.64 | 54.9 |
| 6 | 422 | / | 168 | 47 | 0.36 | 940 | / | 801 | 32.5 | 5.64 | 46.9 |
| 7 | / | 422 | 168 | 47 | 0.36 | 940 | / | 801 | 32.5 | 5.64 | 46.9 |

2. According to the test requirements, make concrete samples according to the following requirements:

(1) According to the concrete proportion, make 18 molds of concrete test block (40 * 40 * 160 mm) (10 for test and 8 for later use).

(2) 18 test blocks (40*40*40 mm) are formed after mixing and screening out stones according to the concrete proportion.

(3) According to the gelation composition and proportion in the concrete proportion, stir the net paste and form 18 test blocks (40*40*40 mm).

After the preparation of the samples, during the 28-day basic cure, samples 1-5 are cured by ordinary cure, and samples 6 and 7 are cured by spraying with 10% limestone powder aqueous solution.

In order to fully consider the influence of external carbonate ion infiltration on concrete performance, two curing methods, standard cure and low-temperature cure, are adopted after 28-day foundation curing.

The standard cure is that at room temperature of 20° C., magnesium sulfate solution and 10% limestone powder aqueous solution are used for flowing infiltration to reach the relative humidity of 95%.

The low-temperature cure is the immersion cure of the test piece in a solution with a temperature of 4-6° C., and the solution is the mixed solution of limestone powder aqueous solution with 10% concentration and magnesium sulfate solution.

3. Analysis of Test Results

After curing, the concrete samples are subjected to mechanical test, apparent and microscopic analysis at 1 month, 3 months, 6 months, 9 months and 12 months respectively, in which the flexural strength is tested by mechanical experimental equipment, and the external surface and internal state are tested by infrared and thermal analysis testing equipment.

Observe the appearance change, take photos and analyze the phenomena such as cracks and structural integrity of the sample, so as to analyze the influence trend of internal damage on the appearance of the samples;

Mechanical test by experimental equipment shows that curing conditions have a certain degree of influence on the strength development of concrete samples. When curing at low temperature, the compressive strength and flexural strength show a downward trend, which is reflected in the corresponding corrosion resistance coefficient, as shown in the following table:

Changes of Mechanical Properties of Samples after Curing at Low Temperature for 6 Months

|  |  | Test number | | | | | | |
| --- | --- | --- | --- | --- | --- | --- | --- | --- |
|  |  | 1 | 2 | 3 | 4 | 5 | 6 | 7 |
| Compressive strength/MPa | Cure in refrigerator at 5° C. | 38.0 | 53.2 | 49.5 | 53.2 | 23.8 | 53.7 | 33.7 |
|  | Standard cure at 20° C. | 46.2 | 54.2 | 70.5 | 77.0 | 59.3 | 68.7 | 73.8 |
| Compressive strength corrosion resistance coefficient/% | | S2.3 | 98.2 | 70.2 | 69.1 | 40.1 | 78.2 | 45.6 |
| Flexural strength/MPa | Cure in refrigerator at 5° C. | 6.9 | 5.2 | 8.8 | 8.4 | 6.4 | 9.6 | 8.3 |
|  | c | 8.0 | 8.3 | 10.1 | 10.6 | 10.0 | 10.0 | 10.6 |
| Flexural strength corrosion resistance coefficient/% | | 86.25 | 62.65 | 87.13 | 79.25 | 64.00 | 96.00 | 78.30 |

Changes of Mechanical Properties of Samples after Curing at Low Temperature for 12 Months

|  |  | Test number | | | | | | |
| --- | --- | --- | --- | --- | --- | --- | --- | --- |
|  |  | 1 | 2 | 3 | 4 | 5 | 6 | 7 |
| compressive strength/MPa | Cure in refrigerator at 5° C. | 27.4 | 23.5 | 35.4 | 40.8 | 25.3 | 37.1 | 40.8 |
|  | Standard cure at 20° C. | 49.6 | 52.9 | 74.0 | 80.6 | 60.0 | 67.1 | 87.3 |
| Compressive strength corrosion resistance coefficient/% | | 55.2 | 44.4 | 47.8 | 50.6 | 42.2 | 55.3 | 46.7 |
| flexural strength/MPa | Cure in refrigerator at 5° C. | 6.1 | 4.3 | 7.2 | 7.1 | 3.4 | 8.4 | 6.8 |
|  | Standard cure at 20° C. | 8.2 | 8.4 | 9.1 | 11.4 | 9.2 | 9.8 | 8.6 |
| flexural strength corrosion resistance coefficient/% | | 74.39 | 51.19 | 79.12 | 62.28 | 36.96 | 85.71 | 79.07 |

Compared with standard cure conditions, low temperature conditions slow down the changes of mechanical properties of samples. For the same samples, the compressive strength, flexural strength and corresponding corrosion resistance coefficient all show a downward trend with the extension of age.

Figure 1B:
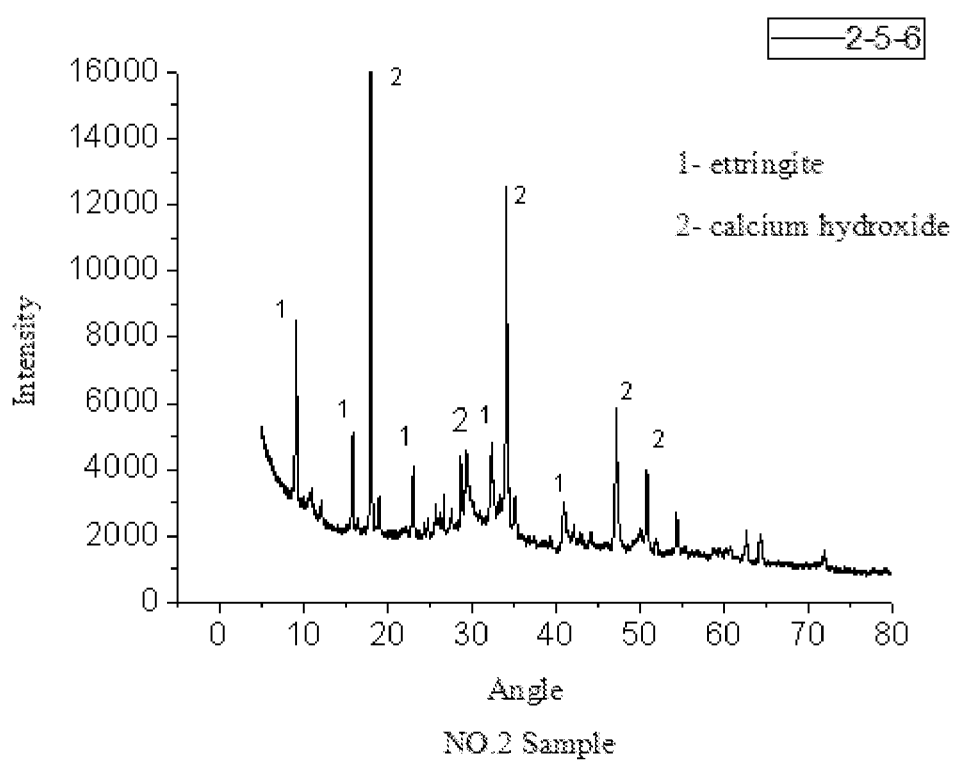
Figure 1C:
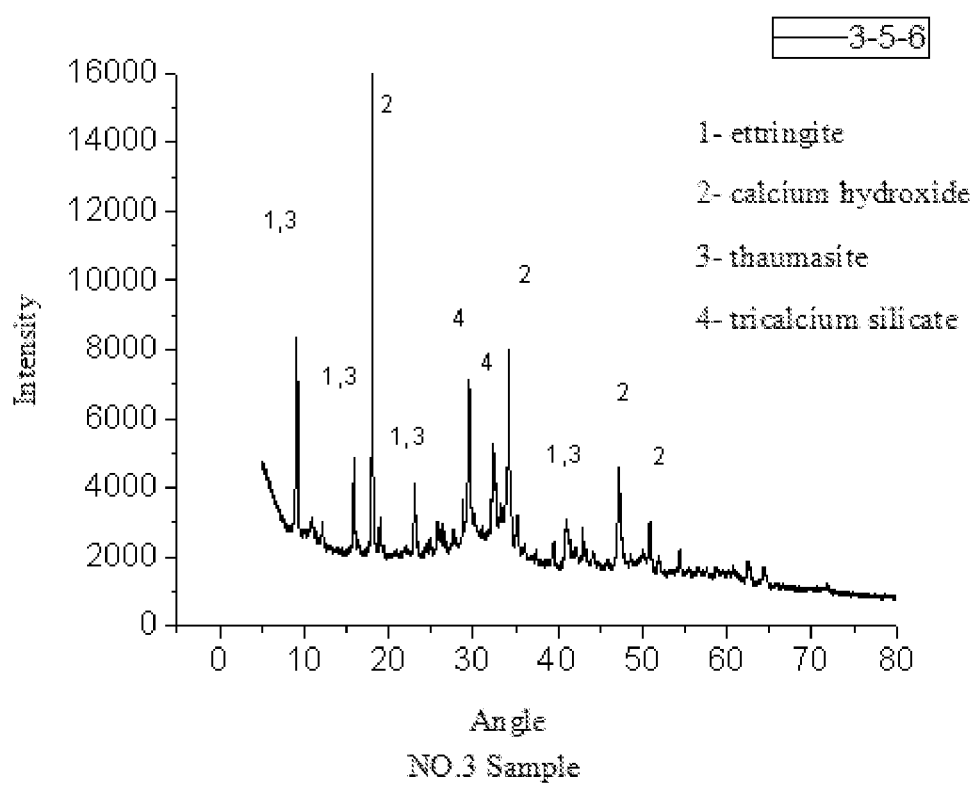
Figure 1D:
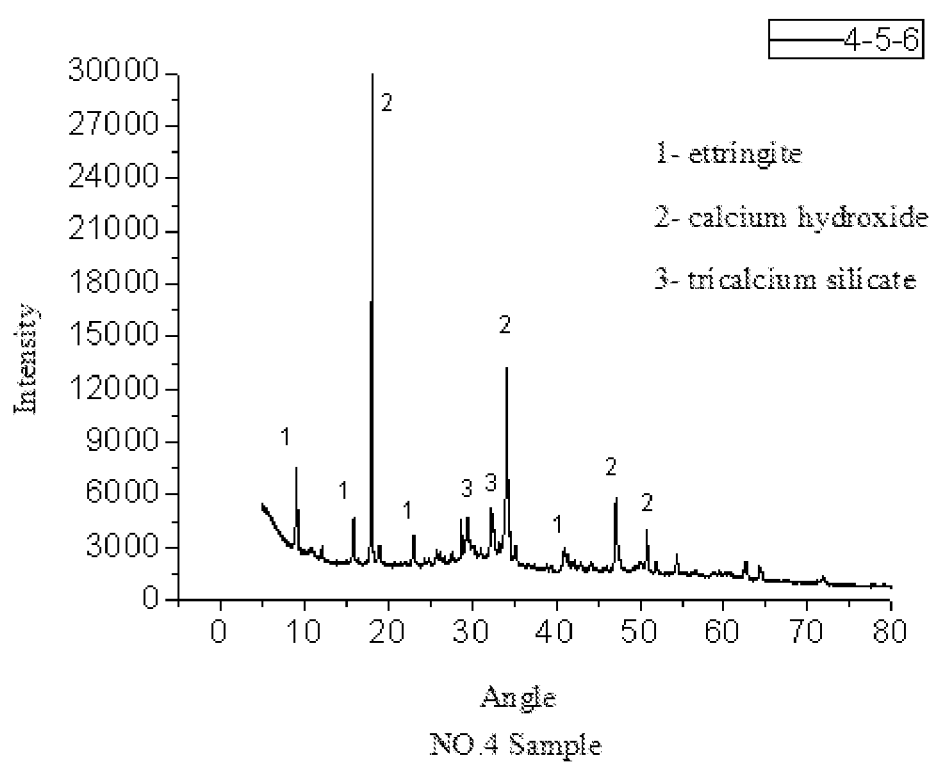
Figure 1E:
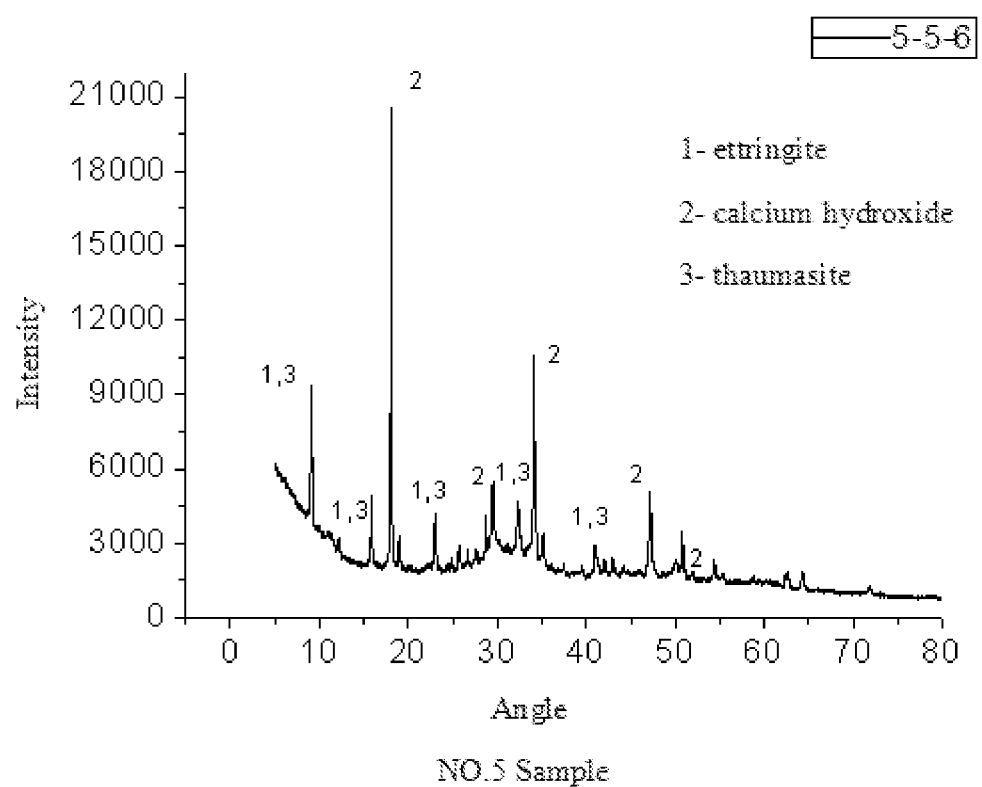
Figure 1F:
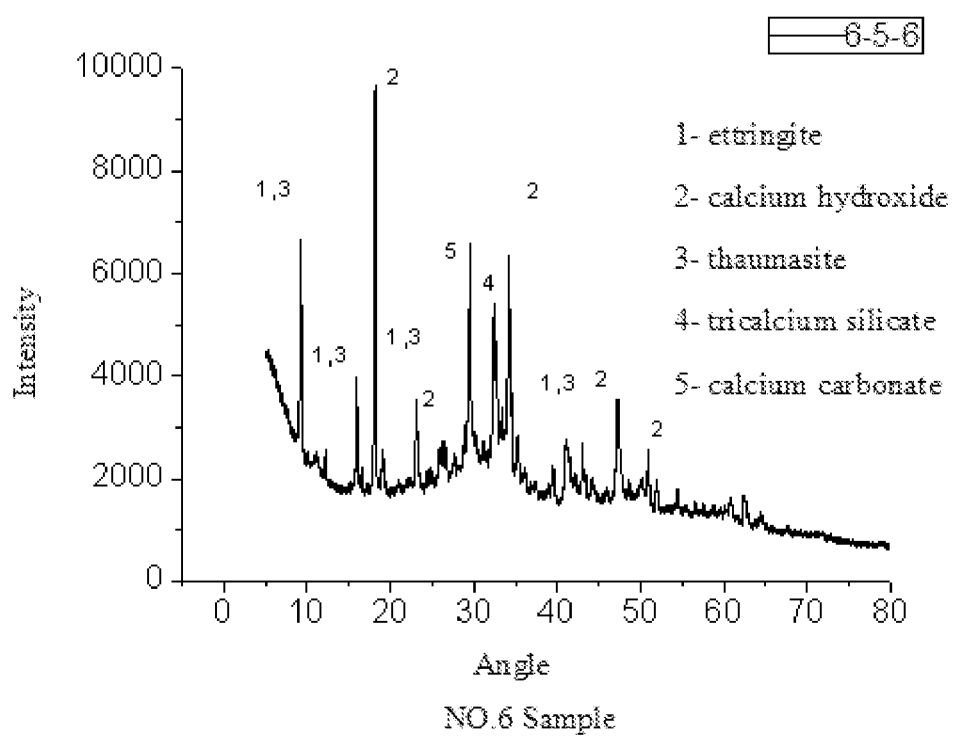
Figure 1G:
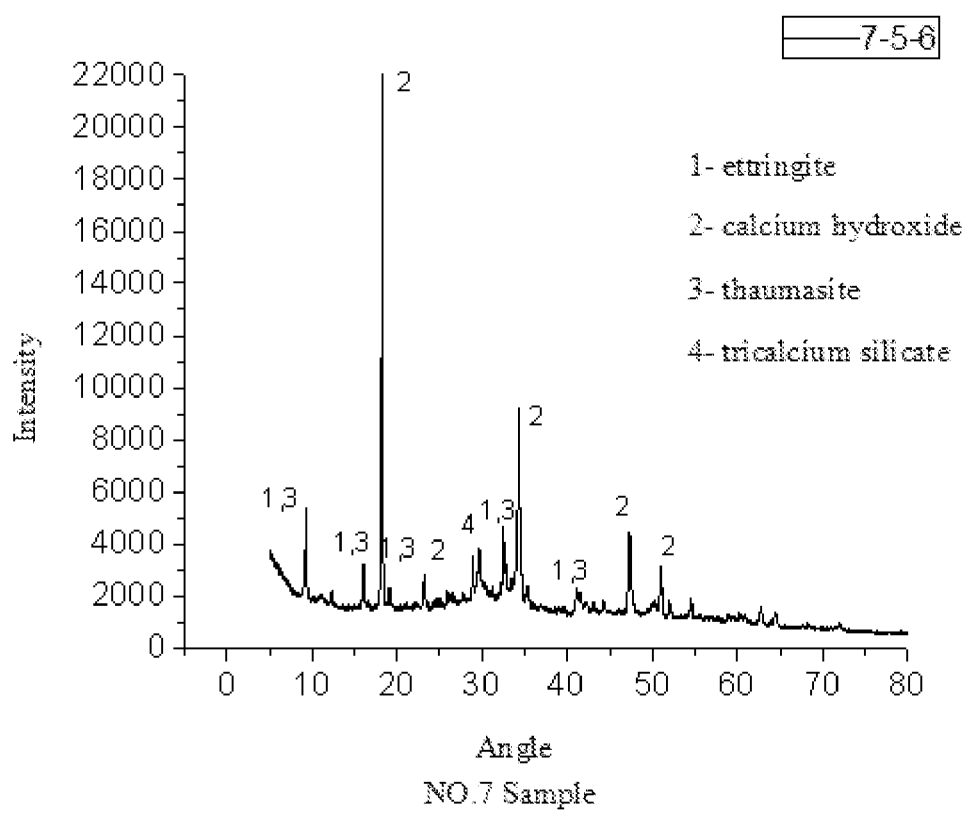
Figure 2A:
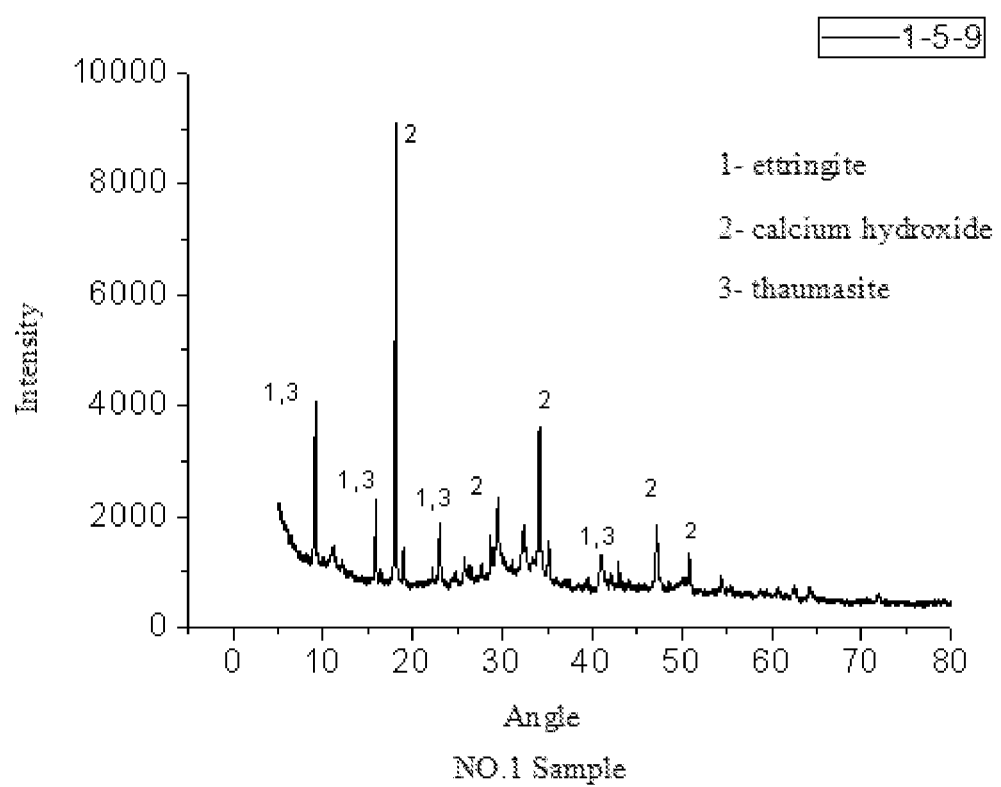
FIG. 2(a-g) is a structural schematic diagram of XRD test results of each sample at the age of 9 months in Embodiment 1 of the present invention.
Figure 2B:
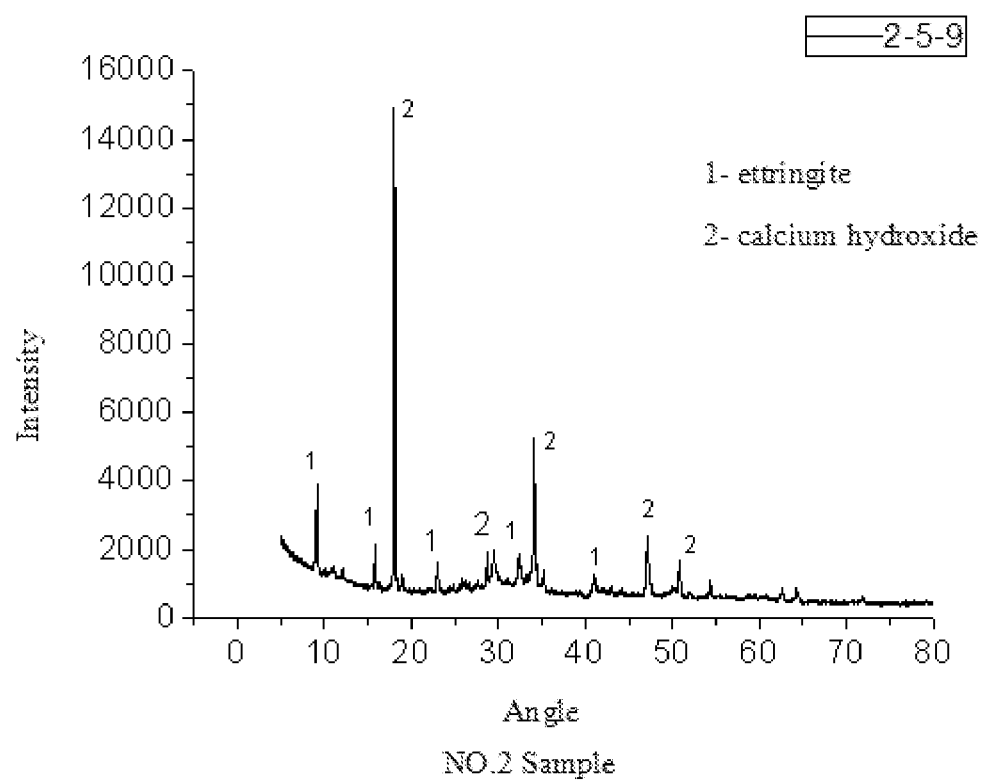
Figure 2C:
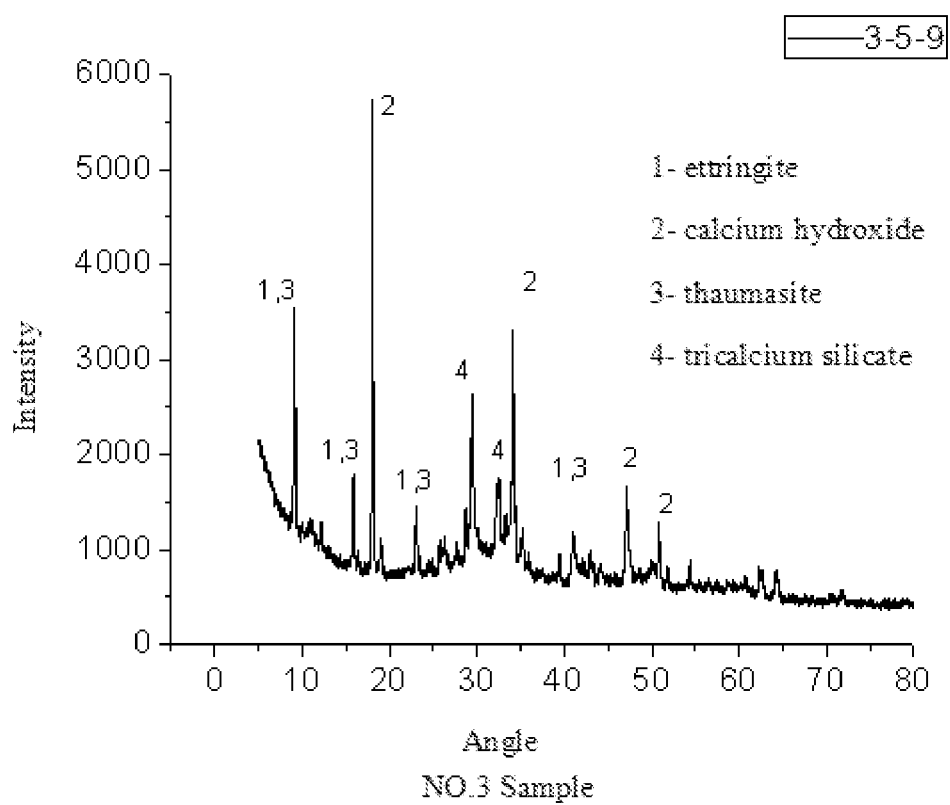
Figure 2D:
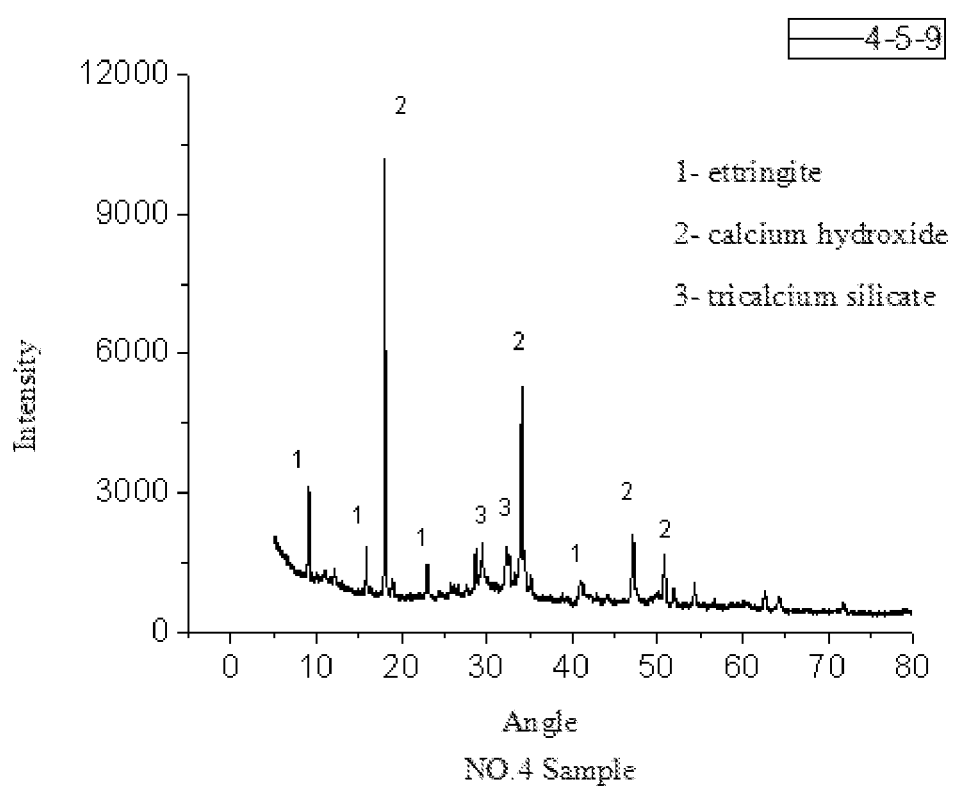
Figure 2E:
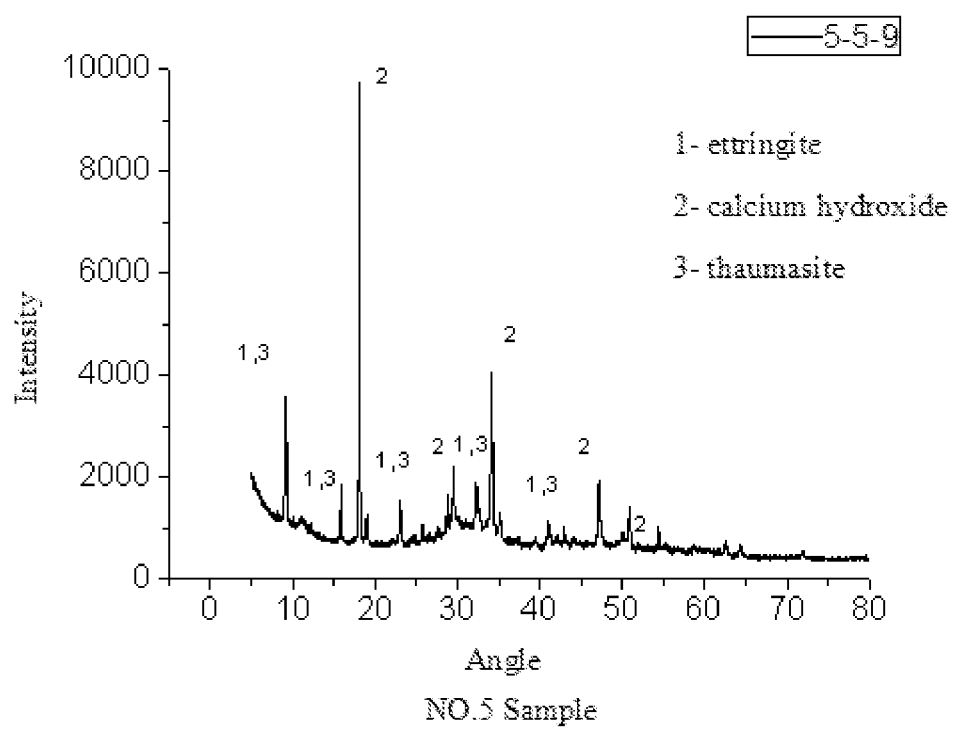
Figure 2F:
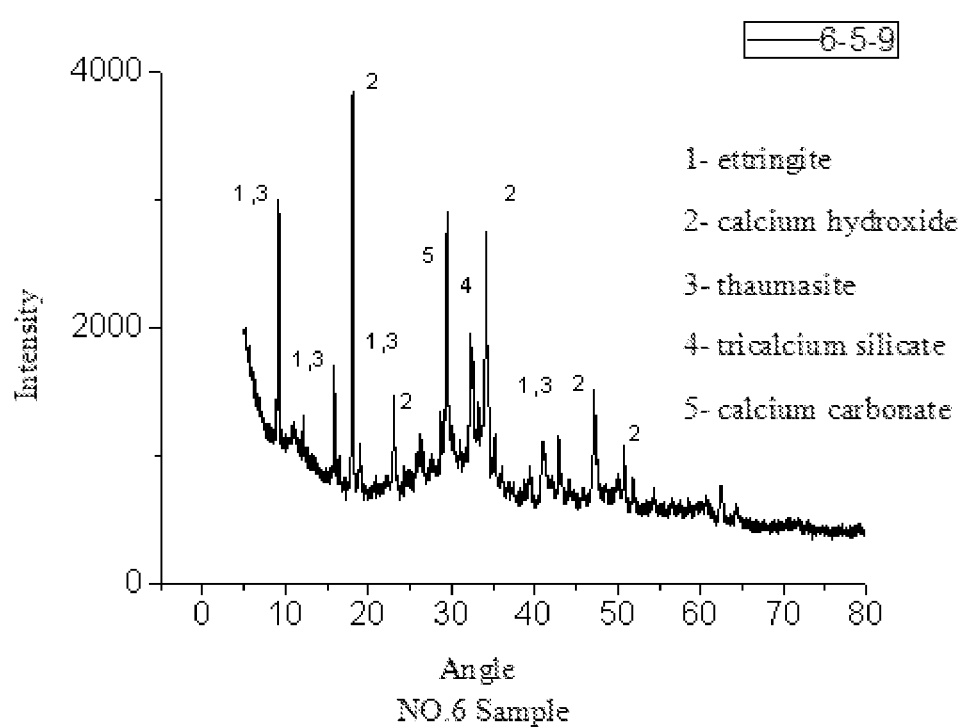
Figure 2G:
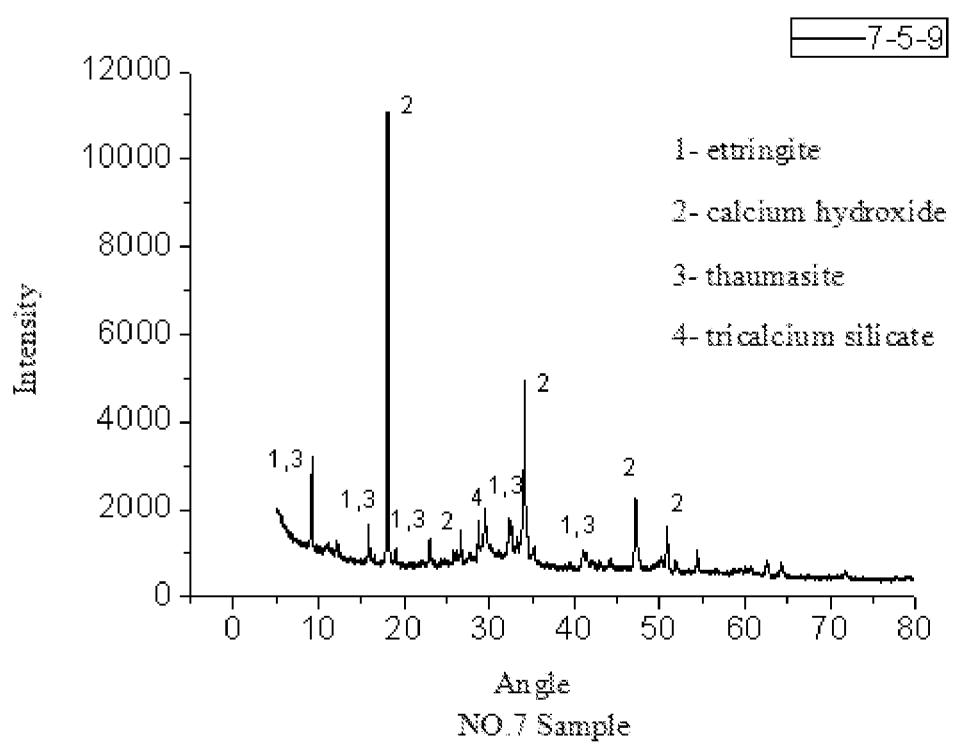
Figure 3A:
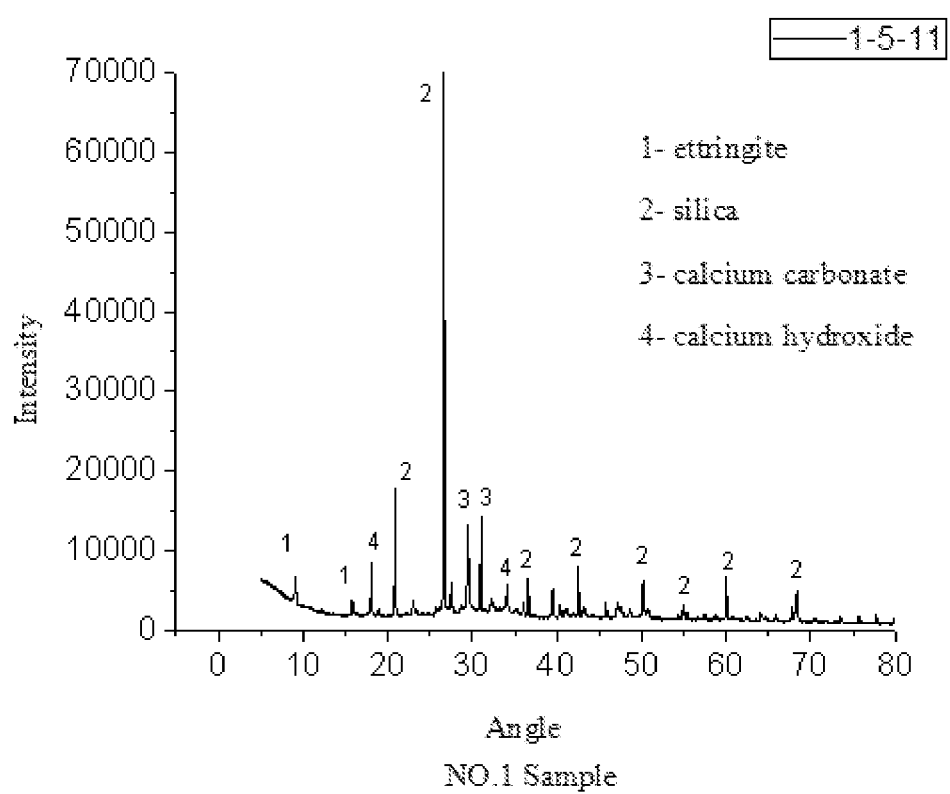
FIG. 3(a-g) is a structural schematic diagram of XRD test results of each sample at the age of 11 months in Embodiment 1 of the present invention.
Figure 3B:
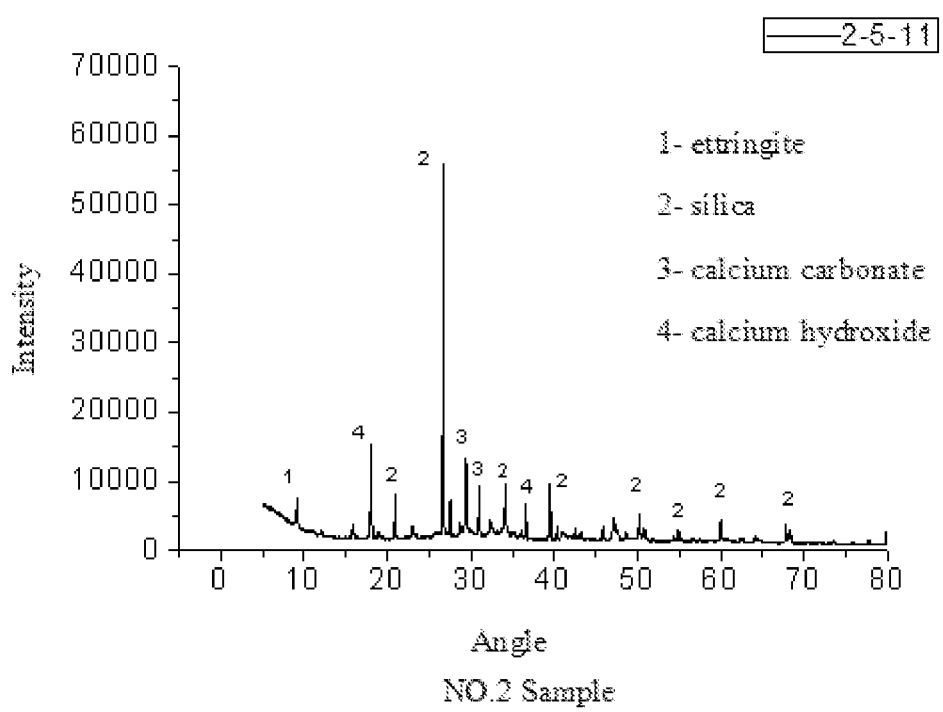
Figure 3C:
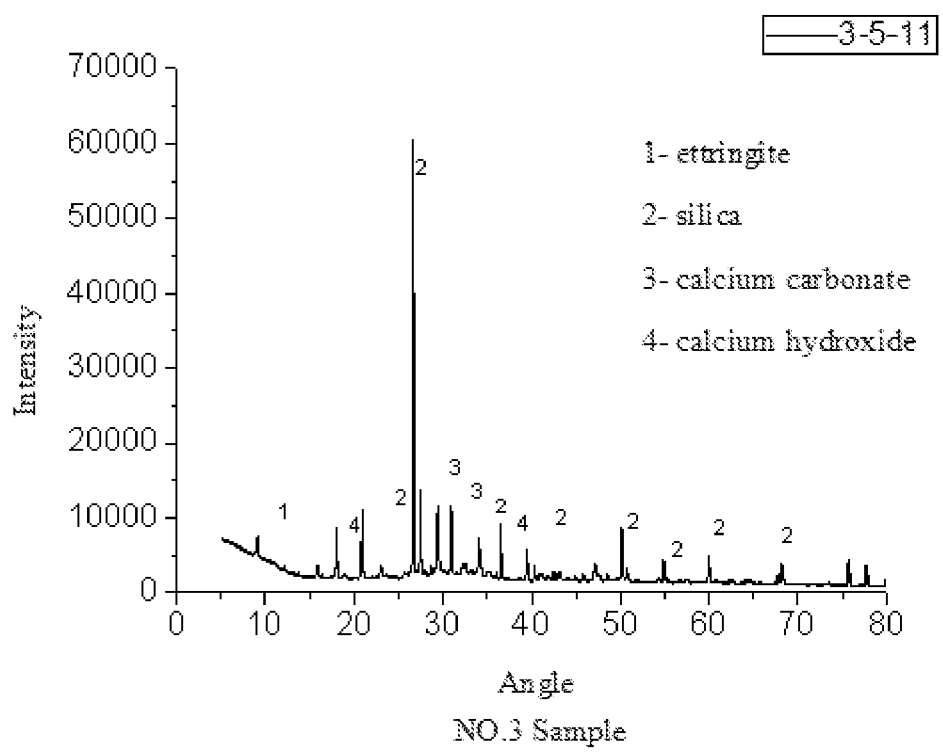
Figure 3D:
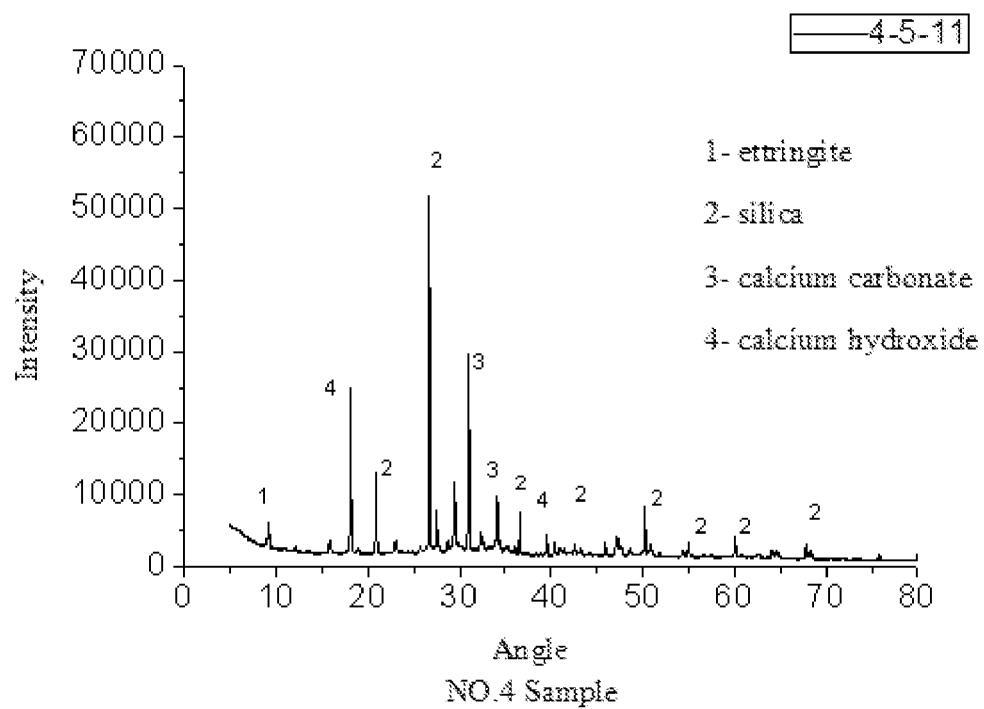
Figure 3E:
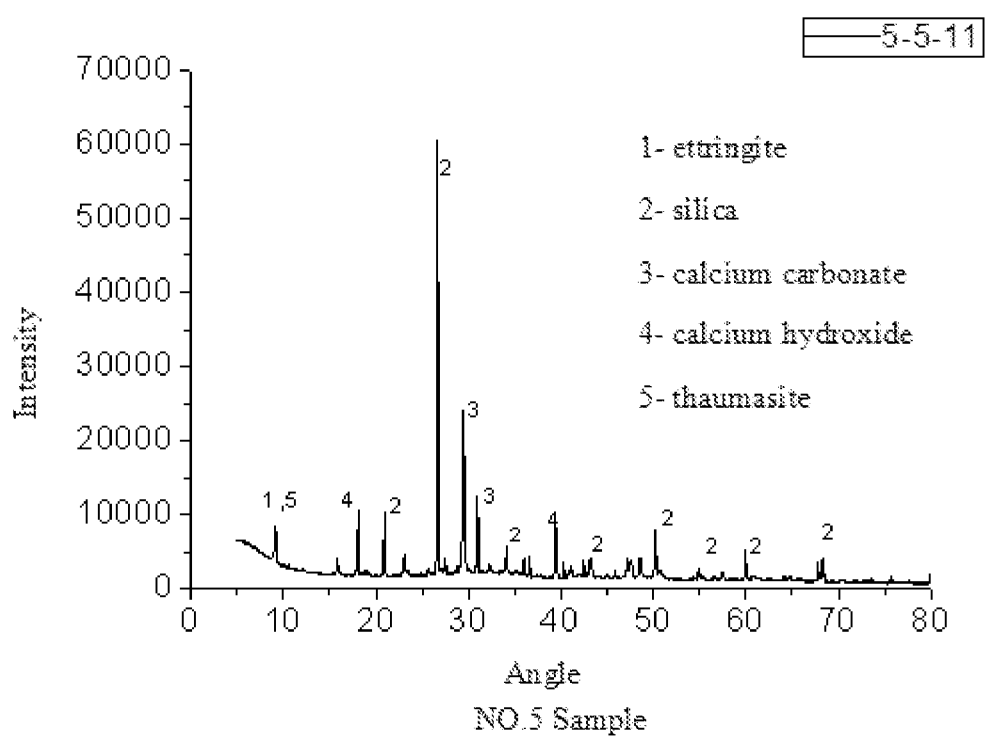
Figure 3F:
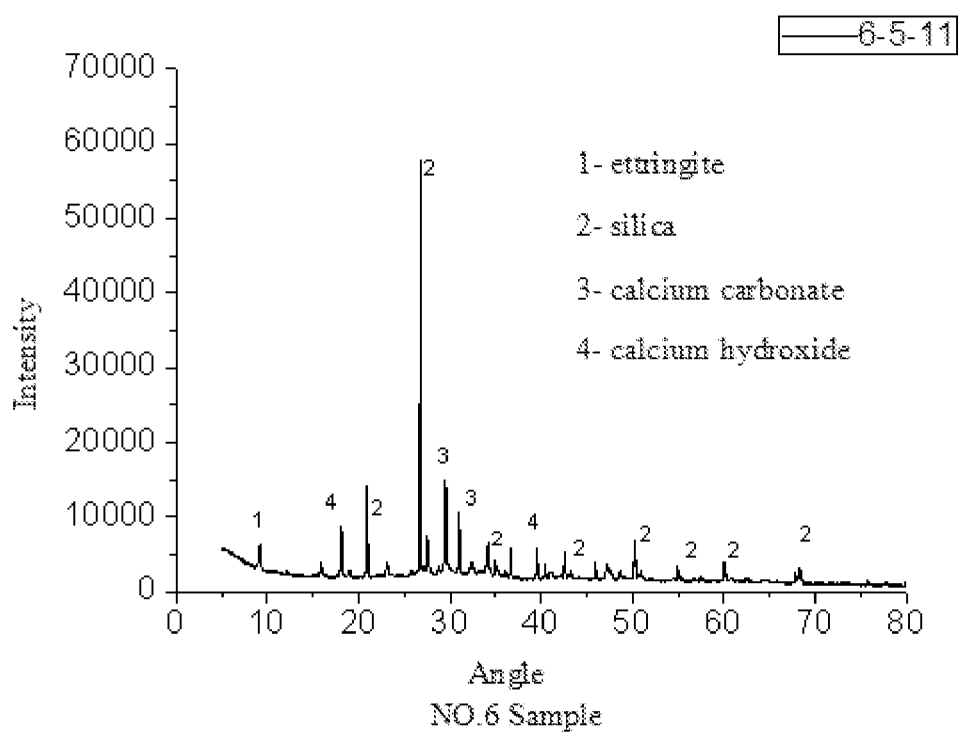
Figure 3G:
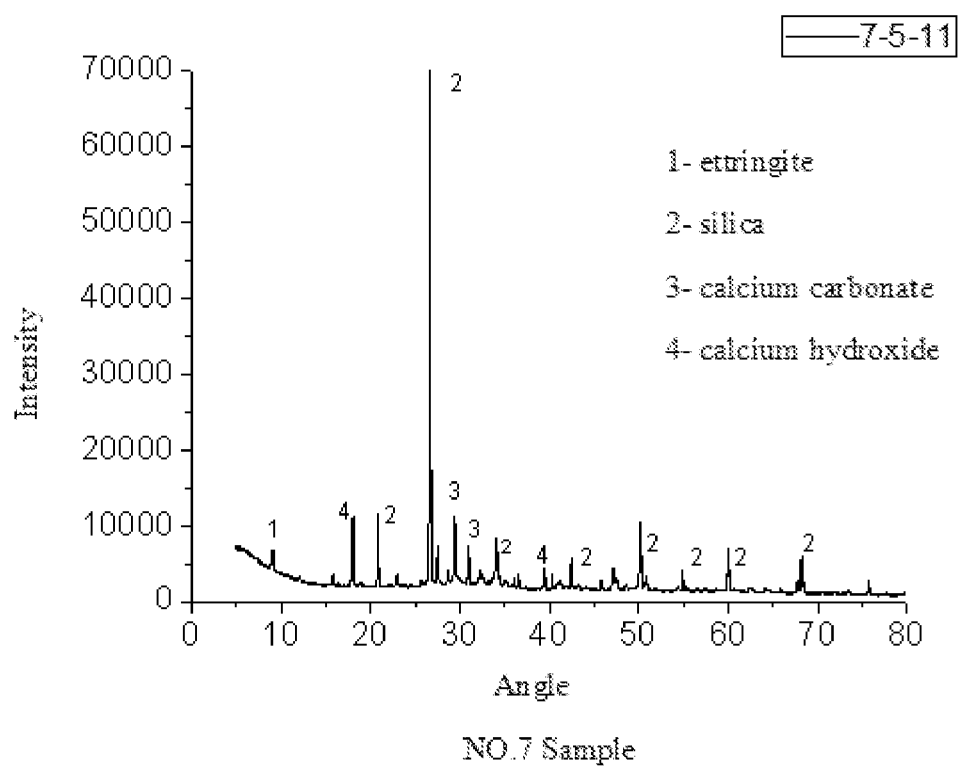
Figure 4A:
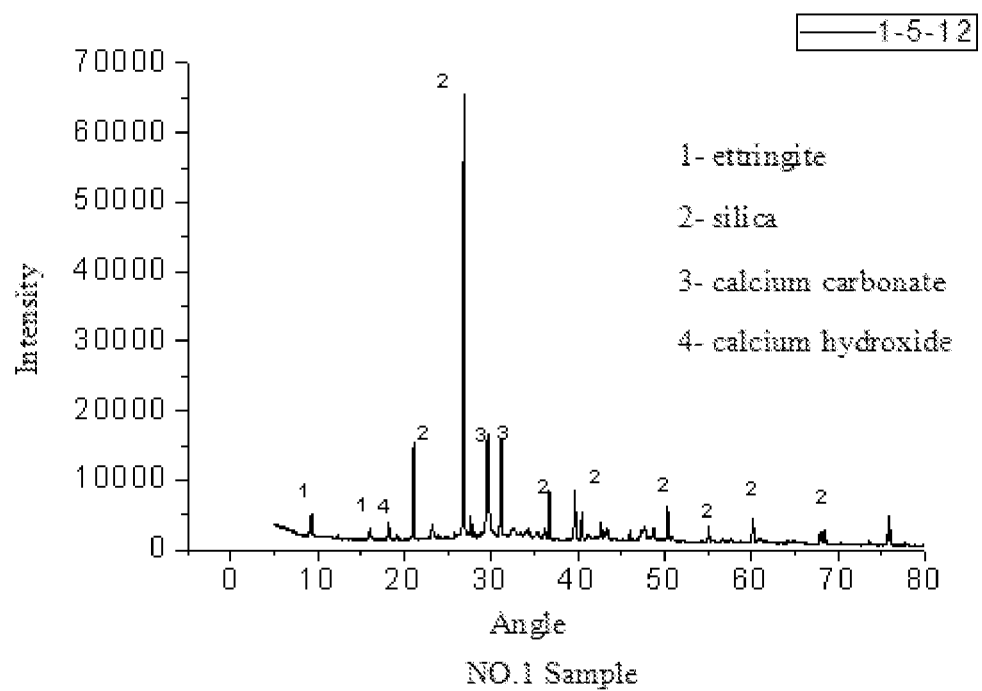
FIG. 4(a-g) is a structural schematic diagram of XRD test results of each sample at the age of 12 months in Embodiment 1 of the present invention.
Figure 4B:
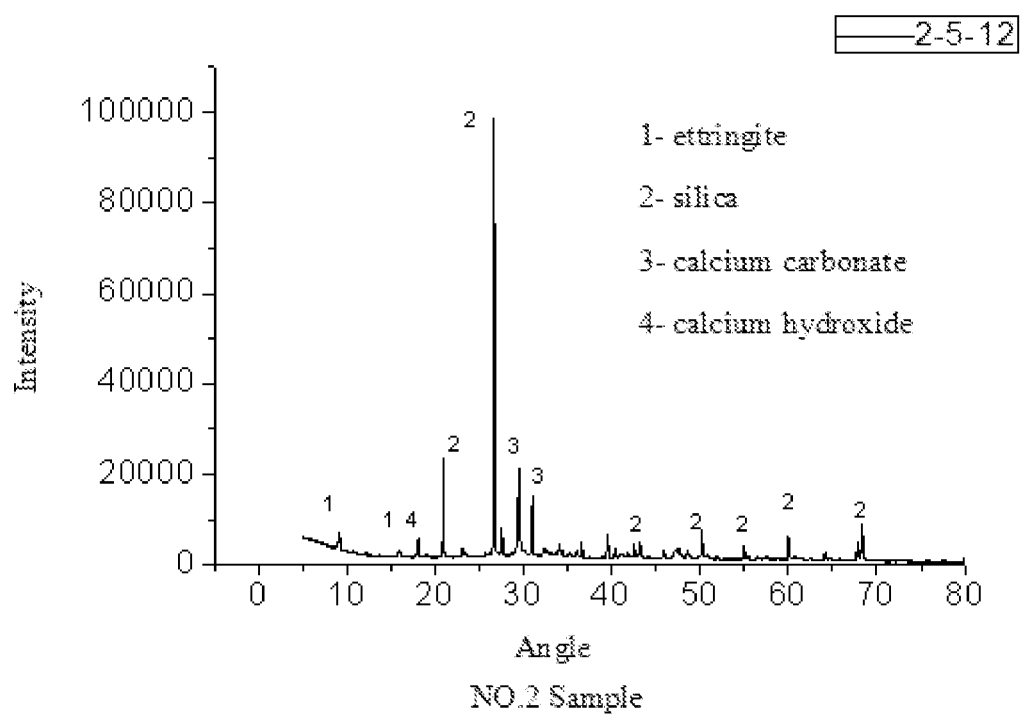
Figure 4C:
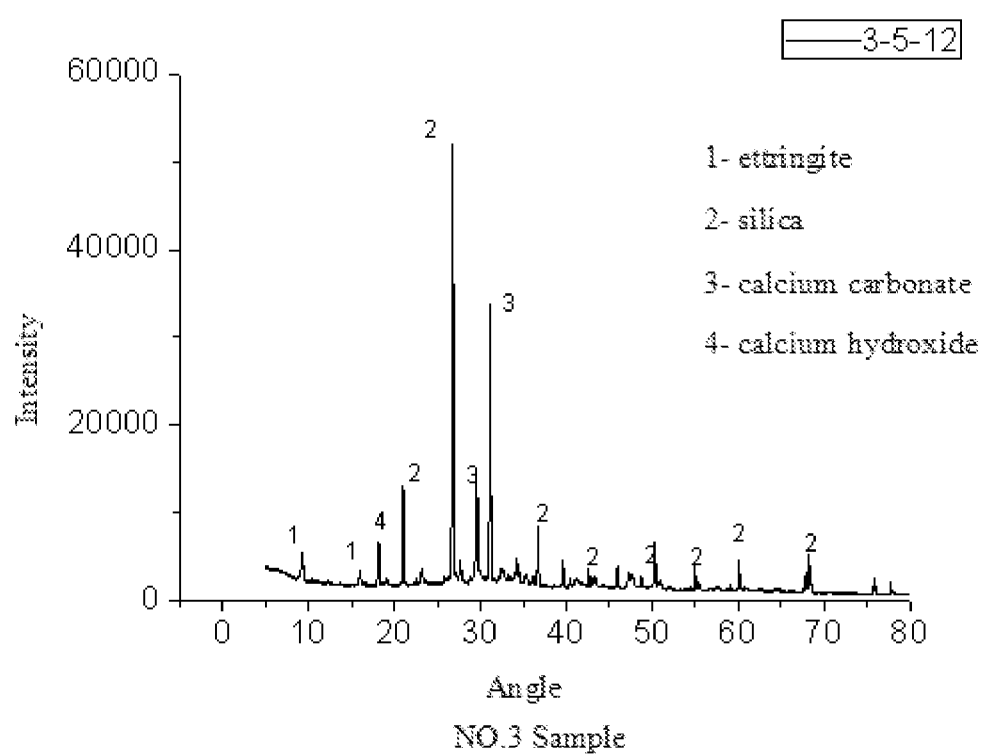
Figure 4D:
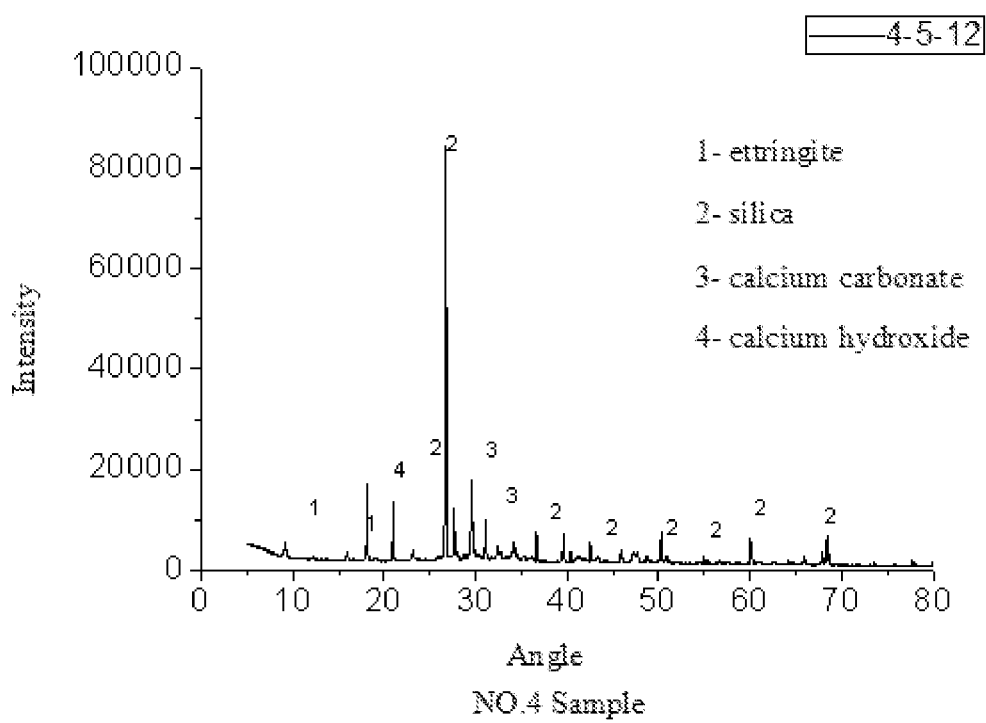
Figure 4E:
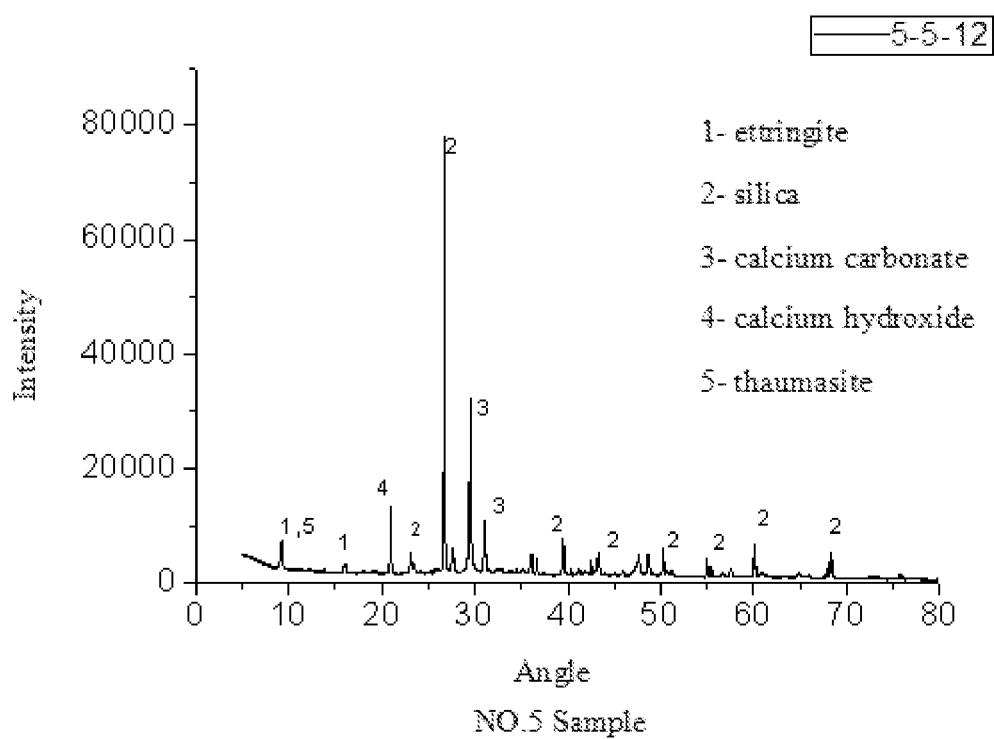
Figure 4F:
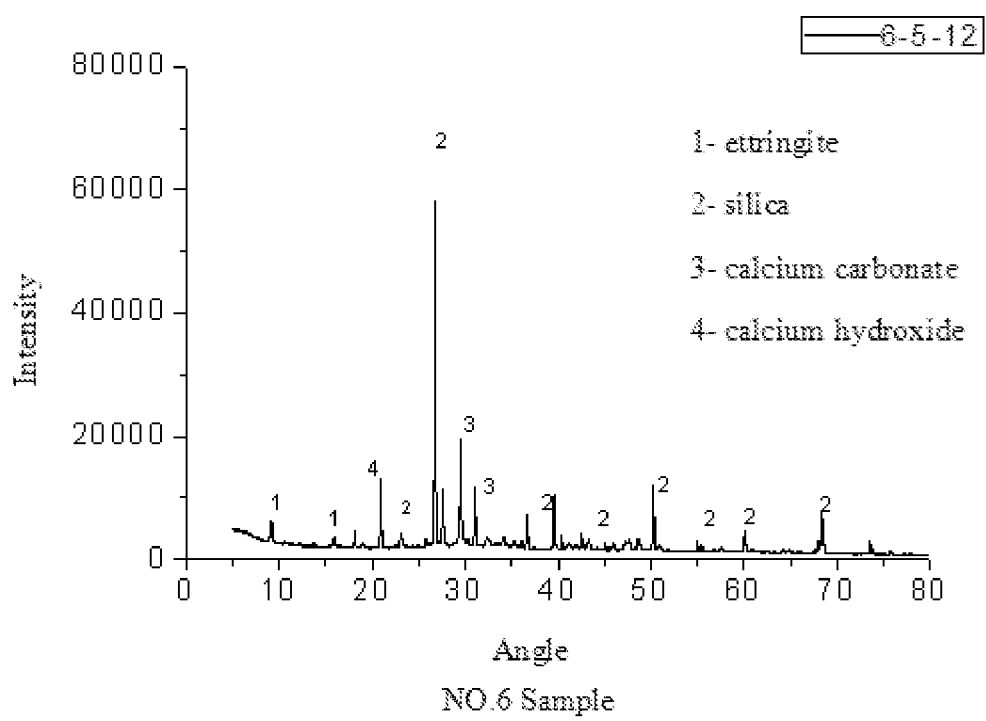
Figure 4G:
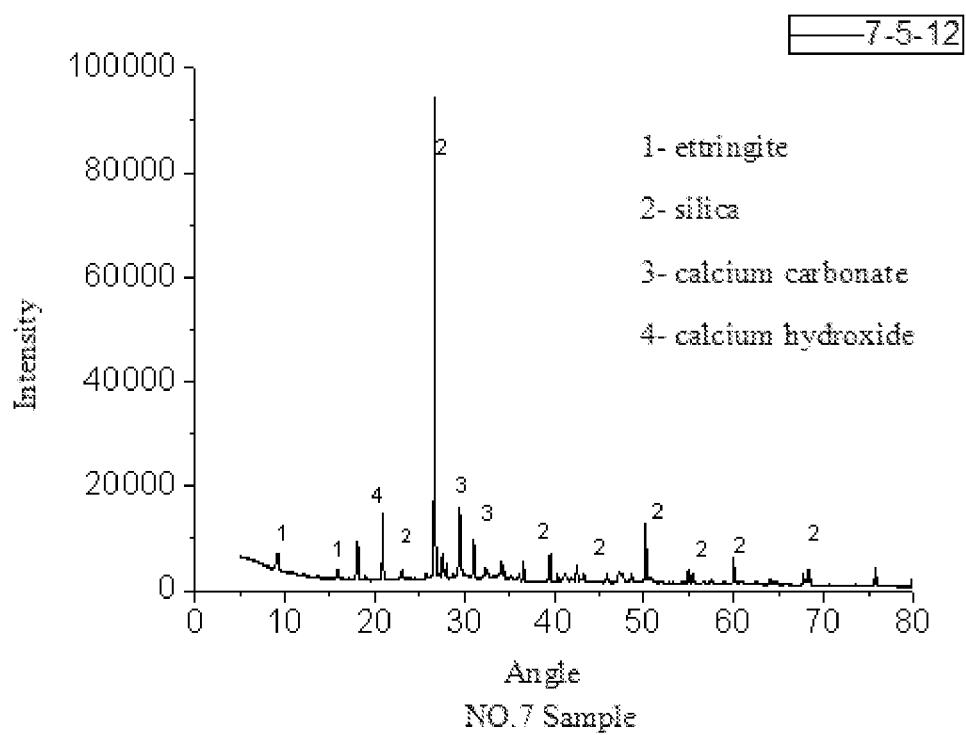

In order to further verify the deep-seated reasons for the appearance change and mechanical property changes of each sample, XRD tests are carried out on samples with different compositions, and the results are shown in FIG. 1(a-g)-FIG. 4(a-g).

Under the experimental conditions, the typical characteristics of TSA damage of No. 5 sample began to appear at 9 months, such as appearance cracks, structural peeling, serious decline of corrosion resistance coefficient, and typical characteristic peaks of TSA found in the XRD results, which indicates that the possibility of TSA damage is high and its resistance is weak.

When soaking for 9 months, the No. 1 sample has obvious sulfate corrosion, but there is no thaumasite in the corrosive. When soaking for 11 months, about 4.11% of thaumasite has appeared in the corrosive. The result shows that if the concrete used in No. 1 sample encounters a high-concentration sulfate environment and its own impermeability is poor, the high-concentration sulfate invading into the concrete will accelerate the sulfate-type corrosion of the concrete.

The comparison between sample No. 2 and No. 5 shows that adding stone powder to concrete material has a significant effect on the formation of thaumasite. The comparison between No. 5 sample and No. 6 sample shows that the influence of external environment carbonate ion on TSA is weak.

Through the comparison of comprehensive test data, it is concluded that No. 4 sample is the best proportion to prevent sulfate corrosion.

The concrete sample is made with the No. 4 component and its proportion, and it is soaked in the box containing gypsum rock, and put into the tunnel until the tunnel construction is finished. The gypsum rock used in the soaking solution of the test block comes from the surrounding rock of the tunnel, and the gypsum content is over 90%. During the test, the appearance changes of concrete are observed in different periods, and the components of corrosive substances are tested and make the XRD spectrum of concrete surface mortar layer with soaking time of 20 months. The test results showed that there is no obvious ettringite and thaumasite in the surface mortar, which indicates that the concrete used for disease treatment had high resistance to sulfate corrosion.

Finally, it should be explained that the above embodiments are only used to illustrate the technical scheme of the present invention, but not to limit it; Although the invention has been described in detail with reference to the foregoing embodiments, it should be understood by those skilled in the art that it can still modify the technical solutions described in the foregoing embodiments, or equivalently replace some or all technical features thereof; these modifications or substitutions do not make the essence of the corresponding technical solutions deviate from the present invention.

What is claimed is:

1. A method for optimizing proportion of sulfate corrosion-resistant concrete, comprising:
    (1) determining compositions and a proportion of a basic sample and a comparison sample according to corrosion characteristics of sulfate and corrosion environment parameters;
    (2) making sample components according to different components and proportions, and carrying out 28-day basic cure, comprising ordinary cure and special cure;
    (3) considering influence of external carbonate ions, setting two samples with a same composition and proportion, and curing the two samples by standard cure and low-temperature cure respectively;
    (4) respectively recording a cure data of the sample in different curing periods;
    (5) observing appearances of the samples, and performing XRD tests to test deep components of the samples; and
    (6) comparing test results and obtaining an optimal composition and proportion of corrosion-resistant concrete according to the test results;
    wherein in the step (3), the standard cure is at room temperature of 20° C., and a magnesium sulfate solution and limestone powder aqueous solution with 10% concentration are used for a flowing infiltration to reach a relative humidity of 95%;
        in the low-temperature cure in the step (3), the samples are placed in a solution with a temperature of 4-6° C. for an immersion cure, and the solution is a mixed solution of the limestone powder aqueous solution with 10% concentration and the magnesium sulfate solution;
    step (1) comprises using corrosion of a thaumasite-type surface to respectively set common samples, optimized cement samples, optimized proportion samples, optimized proportion-optimized cement samples, internally prepared sulfate ion samples, optimized proportion considering carbonate ion intrusion samples and optimized cement considering carbonate ion intrusion samples; and
        the concrete is formed by mixing and stirring base stocks, aggregates, admixtures, external additives and water, and components and mass fractions of the concrete obtained by a method for optimizing proportion are as follows:
    the base stocks are 17.4-17.5 parts of Portland cement with a strength grade of 42.5;
    the aggregates comprise fine aggregates and coarse aggregates, wherein the coarse aggregates are 38.9 parts of basalts with a particle size of 5-10 mm, and the fine aggregates are 33.1-33.2 parts of basalt medium sand;
    the admixtures are 1.9-1.95 parts of silica fume or fly ash with total activity greater than 80%;
    6.9-7 parts of water is added; and
    the external additives are a liquid preservative and a water reducer, the water reducer is 0.23-0.24 part of polycarboxylate water reducer, and the liquid preservative is 1.34-1.35 part of sulfate corrosion-resistant liquid preservative.

2. The method for optimizing proportion of sulfate corrosion-resistant concrete according to claim 1, wherein the components of the samples in the step (1) are set as follows:
    the components of the common sample are as follows: P.O cement with a strength of 42.5, water, fly ash, limestone, basalt medium sand, liquid preservative and water reducer;
    the components of the optimized cement sample are that: based on the common sample, replace the cement in the common sample with P.I cement with a strength of 42.5;
    the components of the optimized proportion sample are as follows: P.O cement with a strength of 42.5, water, fly ash, basalt, basalt medium sand, liquid preservative and water reducer;
    the components of optimized proportion-optimized cement sample are that: based on the optimized proportion sample, replace the cement in the optimized proportion sample with P.I cement with a strength of 42.5; and
    the components of the internally prepared sulfate ion sample are as follows: P.O cement with a strength of 42.5, water, limestone powder, limestone, medium sand and water reducer.

3. A test method for optimizing proportion of sulfate corrosion-resistant concrete according to claim 1, wherein:
    the optimized proportion considering carbonate ion intrusion sample means that the optimized proportion sample is performed spray cure by using the limestone powder aqueous solution with 10% concentration during the 28-day basic cure, and the spray cure is a special cure; and
    the optimized cement considering carbonate ion intrusion sample means that the optimized proportion-optimized cement sample is performed spray cure by using the limestone powder aqueous solution with 10% concentration during the 28-day basic cure, and the spray cure is a special cure.

4. The method for optimizing proportion of sulfate corrosion-resistant concrete according to claim 1, wherein the curing time in the step (4) is 1 month, 3 months, 6 months, 9 months and 12 months respectively.

* * * * *